(12) United States Patent
Kacprowicz

(10) Patent No.: US 11,026,584 B2
(45) Date of Patent: Jun. 8, 2021

(54) HANDHELD DEVICE AND METHOD FOR TOMOGRAPHIC OPTOACOUSTIC IMAGING OF AN OBJECT

(71) Applicant: iThera Medical GmbH, Neuherberg (DE)

(72) Inventor: Marcin Kacprowicz, Unterschleissheim (DE)

(73) Assignee: iThera Medical GMBH, Nueherberg (DE)

( * ) Notice: Subject to any disclaimer, the term of this patent is extended or adjusted under 35 U.S.C. 154(b) by 21 days.

(21) Appl. No.: 14/102,328

(22) Filed: Dec. 10, 2013

(65) Prior Publication Data

US 2014/0221810 A1 Aug. 7, 2014

Related U.S. Application Data

(60) Provisional application No. 61/735,578, filed on Dec. 11, 2012.

(30) Foreign Application Priority Data

Dec. 11, 2012 (EP) ..................................... 12008270

(51) Int. Cl.
*A61B 5/00* (2006.01)
*A61B 8/14* (2006.01)

(52) U.S. Cl.
CPC .............. *A61B 5/0095* (2013.01); *A61B 8/14* (2013.01)

(58) Field of Classification Search
CPC ................................ A61B 5/0095; A61B 8/14
USPC ....................................................... 600/407
See application file for complete search history.

(56) References Cited

U.S. PATENT DOCUMENTS 4,059,098 A * 11/1977 Murdock ............... G10K 11/02
600/437
4,180,792 A 12/1979 Lederman et al.
(Continued)

FOREIGN PATENT DOCUMENTS

EP 133703 3/1985
EP 0459392 2/1991
(Continued)

OTHER PUBLICATIONS

Aguirre et al. A curved array photoacoustic tomography system for small animal imaging. 2007 Proc. SPIE 6437: 64370V-1-64370V-10.*
(Continued)

*Primary Examiner* — Michael J Tsai
*Assistant Examiner* — Patrick M Mehl
(74) *Attorney, Agent, or Firm* — Stoel Rives LLP

(57) ABSTRACT

The present disclosure relates to a handheld device and an according method for optoacoustic imaging of an object, comprising an irradiation unit for irradiating the object with electromagnetic radiation, for example, light, and a detector unit for detecting acoustic, for example, ultrasonic, waves generated in the object upon irradiation with electromagnetic radiation, wherein the detector unit comprises an array of detector elements.
In order to facilitate an acquisition of high-quality tomographic optoacoustic images from different depths within the object at a simple overall design, the handheld device may be provided with a recess, in which the irradiation unit and the array of detector elements are provided, wherein the detector elements are arranged in the recess such that the surface normals of at least a part of the detector elements are directed to a region of interest on or within the object.

26 Claims, 5 Drawing Sheets

(56) References Cited

U.S. PATENT DOCUMENTS

| | | | |
|---|---|---|---|
| 4,255,971 A | 3/1981 | Rosenewaig | |
| 4,343,993 A | 8/1982 | Bining et al. | |
| 4,385,634 A | 5/1983 | Bowen | |
| 4,646,756 A * | 3/1987 | Watmough et al. | 607/154 |
| 4,770,183 A | 9/1988 | Groman et al. | |
| 4,986,275 A | 1/1991 | Ishida et al. | |
| 5,411,730 A | 5/1995 | Kirpotin et al. | |
| 5,524,625 A | 6/1996 | Okazaki et al. | |
| 5,840,023 A | 11/1998 | Oraevsky et al. | |
| 5,924,991 A | 7/1999 | Hossack et al. | |
| 6,070,093 A | 5/2000 | Oosta et al. | |
| 6,102,857 A | 8/2000 | Kruger | |
| 6,102,860 A | 8/2000 | Mooney | |
| 6,173,604 B1 | 1/2001 | Xiang | |
| 6,208,749 B1 | 3/2001 | Gutkowicz-Krusin et al. | |
| 6,216,025 B1 | 4/2001 | Kruger | |
| 6,263,221 B1 | 7/2001 | Chance et al. | |
| 6,424,410 B1 | 7/2002 | Pelosi | |
| 6,428,171 B1 | 8/2002 | Aoki et al. | |
| 6,445,453 B1 | 9/2002 | Hill | |
| 6,477,398 B1 | 11/2002 | Mills | |
| 6,498,492 B1 | 12/2002 | Rezvani | |
| 6,508,770 B1 * | 1/2003 | Cai | G01S 7/5209 600/447 |
| 6,511,433 B1 | 1/2003 | Benjamin | |
| 6,526,298 B1 | 2/2003 | Khalil et al. | |
| 6,567,688 B1 | 5/2003 | Wang | |
| 6,615,063 B1 | 9/2003 | Ntziachristos et al. | |
| 6,641,798 B2 | 11/2003 | Achilefu et al. | |
| 6,662,040 B1 | 12/2003 | Henrichs et al. | |
| 6,700,459 B2 | 3/2004 | Raihn et al. | |
| 6,760,609 B2 | 7/2004 | Jacques | |
| 6,768,265 B1 | 7/2004 | Ives et al. | |
| 7,005,653 B1 | 2/2006 | O'Connell et al. | |
| 7,298,869 B1 | 11/2007 | Abernathy | |
| 7,311,679 B2 * | 12/2007 | Desilets | A61B 8/4281 601/3 |
| 7,510,555 B2 | 3/2009 | Kanzius | |
| 7,515,948 B1 * | 4/2009 | Balberg | A61B 5/0095 600/323 |
| 7,894,885 B2 | 2/2011 | Bartal et al. | |
| 2002/0026106 A1 | 2/2002 | Khalil et al. | |
| 2002/0048077 A1 | 4/2002 | Fukumoto | |
| 2002/0073717 A1 | 6/2002 | Dean | |
| 2002/0163735 A1 | 11/2002 | Detlef et al. | |
| 2002/0193678 A1 | 12/2002 | Kruger | |
| 2003/0018262 A1 * | 1/2003 | Manor | A61B 8/06 600/449 |
| 2003/0023152 A1 | 1/2003 | Abbink et al. | |
| 2003/0135110 A1 | 7/2003 | Leussier | |
| 2004/0054268 A1 | 3/2004 | Esenaliev et al. | |
| 2004/0059265 A1 | 3/2004 | Candy et al. | |
| 2004/0067000 A1 | 4/2004 | Bates et al. | |
| 2004/0127783 A1 | 7/2004 | Kruger | |
| 2004/0176805 A1 | 9/2004 | Whelan | |
| 2004/0181153 A1 | 9/2004 | Hall | |
| 2004/0210126 A1 | 10/2004 | Hajaj et al. | |
| 2004/0232321 A1 | 11/2004 | Miles et al. | |
| 2004/0254457 A1 | 12/2004 | van der Weide | |
| 2005/0150309 A1 | 7/2005 | Beard | |
| 2005/0154308 A1 * | 7/2005 | Quistgaard | A61B 8/4281 600/459 |
| 2005/0175540 A1 | 8/2005 | Oraevsky et al. | |
| 2005/0234319 A1 | 10/2005 | Mandelis et al. | |
| 2006/0058685 A1 | 3/2006 | Fomitchov et al. | |
| 2006/0064001 A1 | 3/2006 | Barbour | |
| 2006/0084861 A1 | 4/2006 | Blank et al. | |
| 2006/0184042 A1 | 8/2006 | Wang et al. | |
| 2006/0256339 A1 | 11/2006 | Lowney et al. | |
| 2006/0264717 A1 * | 11/2006 | Pesach et al. | 600/310 |
| 2007/0015992 A1 | 1/2007 | Filkins et al. | |
| 2007/0152144 A1 | 7/2007 | Quake | |
| 2007/0197886 A1 | 8/2007 | Naganuma et al. | |
| 2007/0238954 A1 | 10/2007 | White et al. | |
| 2007/0238958 A1 | 10/2007 | Oraevsky et al. | |
| 2007/0274580 A1 | 11/2007 | Ntziachristos et al. | |
| 2008/0071172 A1 * | 3/2008 | Bruck | A61B 5/0059 600/438 |
| 2008/0118934 A1 | 5/2008 | Gerdes | |
| 2008/0123083 A1 | 5/2008 | Wang et al. | |
| 2008/0173093 A1 | 7/2008 | Wang et al. | |
| 2008/0221647 A1 | 9/2008 | Chamberland et al. | |
| 2008/0228073 A1 * | 9/2008 | Silverman et al. | 600/437 |
| 2009/0024038 A1 | 1/2009 | Arnold | |
| 2009/0038375 A1 * | 2/2009 | Breuer et al. | 73/24.02 |
| 2009/0054763 A1 | 2/2009 | Wang et al. | |
| 2009/0058746 A1 | 3/2009 | Delgado | |
| 2009/0081122 A1 | 3/2009 | Rufenacht et al. | |
| 2009/0192358 A1 | 7/2009 | Jaffer et al. | |
| 2009/0324048 A1 | 12/2009 | Leevy | |
| 2010/0022866 A1 | 1/2010 | Feke et al. | |
| 2010/0078576 A1 | 4/2010 | Ntziachristos et al. | |
| 2010/0249570 A1 | 9/2010 | Carson et al. | |
| 2011/0001975 A1 | 1/2011 | Razansky et al. | |
| 2011/0040176 A1 | 2/2011 | Razansky et al. | |
| 2011/0201914 A1 * | 8/2011 | Wang | A61B 5/0059 600/407 |
| 2011/0208057 A1 | 8/2011 | Oikawa | |
| 2011/0231160 A1 | 9/2011 | Suzuki | |
| 2011/0282192 A1 | 11/2011 | Axelrod et al. | |
| 2011/0301453 A1 | 12/2011 | Ntziachristos et al. | |
| 2011/0306857 A1 | 12/2011 | Razansky et al. | |
| 2011/0306865 A1 | 12/2011 | Thornton et al. | |
| 2012/0029829 A1 | 2/2012 | Li et al. | |
| 2012/0123256 A1 | 5/2012 | Razansky et al. | |
| 2012/0150012 A1 | 6/2012 | Fujimoto et al. | |
| 2012/0220851 A1 | 8/2012 | Razansky et al. | |
| 2012/0238873 A1 | 9/2012 | Lacoste et al. | |
| 2013/0041267 A1 | 2/2013 | Ntziachristos et al. | |
| 2013/0312526 A1 | 11/2013 | Oishi | |
| 2014/0114187 A1 | 4/2014 | Rozental et al. | |
| 2014/0163353 A1 | 6/2014 | Razansky et al. | |
| 2014/0198606 A1 | 7/2014 | Morscher et al. | |
| 2014/0221810 A1 | 8/2014 | Kacprowicz | |
| 2014/0336505 A1 | 11/2014 | Ripoll Lorenzo et al. | |
| 2014/0363066 A1 | 12/2014 | Ntziachristos et al. | |

FOREIGN PATENT DOCUMENTS

| | | |
|---|---|---|
| EP | 1561424 | 8/2005 |
| EP | 2695893 | 8/2012 |
| JP | 09219563 | 8/1997 |
| JP | 2004351023 | 12/2004 |
| JP | 2007/307007 | 11/2007 |
| JP | 2010125260 | 6/2010 |
| JP | 2012170762 | 9/2012 |
| WO | WO2004/068405 | 8/2004 |
| WO | WO2006/061829 | 6/2006 |
| WO | WO2006/063246 | 6/2006 |
| WO | WO2007/084771 | 7/2007 |
| WO | WO2007/100937 | 9/2007 |
| WO | WO2007/111669 | 10/2007 |
| WO | WO2008/018082 | 2/2008 |
| WO | WO2008/101019 | 8/2008 |
| WO | WO2009/055095 | 4/2009 |
| WO | WO2010/009747 | 1/2010 |
| WO | WO2011/000389 | 1/2011 |
| WO | WO2011/072198 | 6/2011 |
| WO | WO2011/137385 | 11/2011 |
| WO | WO2012/108170 | 8/2012 |
| WO | WO2012/108172 | 8/2012 |
| WO | WO2012/137855 | 10/2012 |
| WO | WO2012/150721 | 11/2012 |
| WO | WO2013/185784 | 12/2012 |
| WO | WO2013/167147 | 11/2013 |
| WO | WO2014/066150 | 5/2014 |

OTHER PUBLICATIONS

Allen et al. Dual wavelength laser diode excitation source for 2D photoacoustic imaging. 2007 Proc. SPIE 6437: 74371U-1-64371U-9.*

(56) References Cited

OTHER PUBLICATIONS

Song. High-speed photoacoustic microscopy in vivo. 2010 Ph.D. thesis, School of Eng. & Appl. Sci., Washington University, Saint Louis, 133 pages.*
Viator et al. Clinical testing of a photoacoustic probe for port-wine stain depth determination. 2002 Lasers Surg. Med. 30:141-148.*
Carotenuto et al. 2002 IEEE Trans. Ultrason. Ferroelec. Freq. Cont. 49:1039-1049.*
Clement et al. 2000 Phys. Med. Biol. 45:3707-3719.*
Yao et al. 2011 Contrast Media Mol. Imaging 6:332-345.*
Fronheiseretal. 2010 Journal of Biomedical Optics 15:021305-1-021305-7 (Year: 2010).*
Andreev et al. from IDS 2002 Proc. SPIE 4618:137-145 (Year: 2002).*
Andreev et al. 2000 Proc. SPIE 3916:36-47 (Year: 2000).*
U.S. Appl. No. 14/102,250, filed Dec. 10, 2013, Razansky et al.
Ash et al., 'Super-Resolution Aperture Scanning Microscope', Nature, vol. 237, Jun. 30, 1972, pp. 510-512.
Razansky et al., 'Hybrid Photoacoustic Fluorescence Molecular Tomography Using Finite-Element-Based Inversion', Med Phys, Nov. 2007, vol. 34 No. 11, pp. 4293-4301.
Larin et al., 'Monitoring of Tissue Coagulation During Thermotherapy Esing Optoacoustic Technique', Journal of Physics D: Applied Physics, 2005, vol. 38, pp. 2645-2653.
'American National Standard for Safe Use of Lasers', Laser Institute of America, ANS1Z136.1, 2007 (revision of ANS1Z136.1 2000).
Laufer et al., 'Quantitative Spatially Resolved Measurement of Tissue Chromophore Concentrations Using Photoacoustic Spectroscopy: Application to the Measurement of Blood Oxygenation and Haemoglobin Concentration', Phys Med Biol, 2007, vol. 52, pp. 141-168.
Chen et al., 'Atomic Decomposition by Basis Pursuit', SIAM Review, 2001, vol. 43 No. 1, pp. 129-159.
Jetzfellner et al., 'Preformance of Interactive Optoacoustic Tomography with Experimental Data', Applied Physics Letters, 2009, vol. 95, pp. 013703.1-013703.3.
Cox et al., 'Gradient-Based Quantitative Photoacoustic Image for Molecular Imaging', Proc of SPIE, 2007, vol. 6437, pp. 643IT.1-643IT.10.
Cox et al., 'Two-Dimensional Quantitative Photoacoustic Image Reconstruction of Absorption Distributions in Scattering Medica by Use of a Simple Iterative Method', Applied Optics, Mar. 10, 2006, vol. 45 No. 8, pp. 1866-1873.
Paltauf et al., 'Iterative Reconstruction Algorithm for Optoacoustic Imaging', J Acoust Soc Am, Oct. 2002,vol. 112 No. 4, pp. 1536-1544.
Jiang et al., 'Spatially Varying Optical and Acoustic Property Reconstruction Using Finite-Element-Based Photoacoustic tomography', J Opt Soc Am, Apr. 2006, Vo. 23 No. 4, pp. 878-888.
Intes et al. 'Projection Access Order in Algebraic Reconstruction Technique for Diffuse Optical Tomography', Phys Med Biol, 2002, vol. 47, pp. N1-N10.
Office Action dated Dec. 7, 2012 for U.S. Appl. No. 13/055,552.
Vinegoni et al., 'In vivo Imaging of Drosophila Metanogaster Pupae with Mesoscopic Fluorescence Tomography', Nature Methods, Jan. 2008, vol. 5 No. 1, pp. 45-47 and Supplementary Notes.
Zacharakis et al., 'Volumetric Tomography of Fluorescent Proteins Through Small Animals In Vivo', PNAS, Dec. 20, 2005, vol. 102 No. 51, pp. 18252-18257.
Capps, "Near Field or Far Field?", EDN Network, www.ednmag.con Aug. 16, 2001, p. 95-102.
Office Action dated Jun. 3, 2013 for U.S. Appl. No. 12/867,265.
Office Action dated Jun. 18, 2013 for U.S. Appl. No. 13/055,552.
Office Action dated Aug. 2, 2013 for U.S. Appl. No. 13/386,491.
Yuan et al., 'Quantitative Photoacoustic Tomography: Recovery of Optical Absorption coefficient Maps of Haterogeneous Media', Applied Physics Letters 88:231101, 2006.
Razansky et al., 'Multispectral Photoacoustic Imaging of Fluorochromes in Small Animals', Optics Letters, vol. 32, No. 19, pp. 2891-2893, Oct. 1, 2007.
Rosenthal et al., 'Quantitative Optoacoustic Signal Extraction Using Sparse Signal Repesentation', IEEE Transactions on Medical Imaging, vol. 28, No. 12, pp. 1997-2006, 2009.
Xu et al., 'Exact Frequency-Domain Reconstruction for Thermoacoustic Tomography—I: Planar Geometry', IEEE Transactions on Medical Imaging, vol. 21, No. 7, pp. 823-828, 2002.
Oraevsky et al., 'Direct Measurement of Laser Fluence Distribution and Optoacoustic Imaging in Heterogeneous Tissues', Proc SPIE 2323, Laser Interactions with Hard and Soft Tissue 11, 37, 1995.
Karabutov et al., 'Optoacoustic Measurement of Optical Properties of Turbid Media', Proc. SPIE vol. 4749, pp. 288-298, 2002.
Razansky et al., 'Multispectral Opto-Acoustic Tomography of Deep-Seated Fluorescent Proteins in Vivo', Nature Photonics, 3, 412-417, 2009.
Schulz et al., 'Experimental Fluorescence Tomography of Tissues with Noncontact Measurements', IEEE Transactions on Medical Imaging, Vo. 23, No. 4, oo 492-500, 2004.
Ripoll et al., 'Free-Space Propagation of Diffuse Light: Theory and Experiments', Phys. Rev, Lett., vol. 91, No. 10, pp. 103901-1-103901-6, 2003.
Zibulevsky et al., 'Blind Source Separation by Sparse Decomposition', ICA, Principle and Practice, Chapter 7, Cambridge, 2001.
Office Action dated Oct. 6, 2014 for U.S. Appl. No. 13/381,207.
Office Action dated Oct. 29, 2014 for U.S. Appl. No. 13/055,552.
U.S. Appl. No. 13/399,272, filed Nov. 6, 2014, Kellnberger et al.
Office Action dated Nov. 26, 2014 for U.S. Appl. No. 13/386,491.
Office Action dated Dec. 26, 2014 for U.S. Appl. No. 12/867,265.
Xu et al., 'Universal Back-Projection Algorithm for Photoacoustic Computed Tomography', The American Physical Society,Physical Review, vol. E71, No. 1, pp. 016706, 2005.
Skolnik, Radar Handbook, McGraw Hill, Chapter 8, 2008.
Ye, 'PSTD Method of Thermoacoustic Tomography (TAT) and Related Experimental Investigation', Dissertation, 2009.
Telenkov et al., 'Frequency-Domain Photothermoacoustics: Alternative Imaging Modality of Biological Tissues', Journal of Applied Physics, vol. 105, p. 102029, 2009.
Fan et al., 'Development of a Laser Photothermoacoustic Frequency-Swept System for Subsurface Imaging: Theory and Experiment', J. Acoust. Soc. Am., 116(6), 2004.
Skolnik, Introduction to Radar Systems, Chapter 6.5, McGraw Hill, 2001.
Skolnik, Introduction to Radar Systems, Chapter 11.5, McGraw Hill, 1981.
Rosenthal et al., 'Fast Semi-Analytical Model-Based Acoustic Inversion for Quantitative Optoacoustic Tomography', IEEE Transactions on Medical Imaging, vol. 29, No. 6, Jun. 2010.
Baddour, 'Theory and Analysis of Frequency-Domain Photoacoustic Tomography', J. Acoust. Soc. Am., 123(5), pp. 2577-2590, 2008.
Paltauf et al., 'Three-Dimensional Photoacoustic Tomography Using Acoustic Line Detectors', Soc. Opt. Eng., vol. 6437,pp. 1-10, 2007.
Maslov et al., 'Photoacoustic Imaging of Biological Tissue with Intensity-Modulated Continuous-Wave Laser', Journal of Biomedical Optics, vol. 13, No. 2, pp. 024006, 2008.
Kak et al., 'Principles of Computerized Tomographic Imaging', IEEE Press, Chapters 3 and 6, 1988.
International Preliminary Report dated Dec. 24, 2014 for PCT/EP2012/002466.
Wang, 'Multiscale Photoacoustic Microscopy and Computed Tomography', Nature Photonics, Review Article, 2009.
Zhang et al., 'Collecting Back-Reflected Photons in Photoacoustic Microscopy', Optics Express, vol. 18, No. 2, Jan. 18, 2010.
Wang et al., 'Photoacoustic Tomography: In Vivo Imaging from Organelles to Organs', Science, 335(6075), Mar. 23, 2012.
Yao et al.; 'Photoacoustic Tomography: Fundamentals, Advances and Prospects', contrast Media Mol Imaging 6(5), 2011.
Li et al., 'Fast-Scanning Reflection-Mode Integrated Photoacoustic and Optical-coherence Microscopy', Proc. Of SPIE, vol. 7564, 2010.
Ntziachristos, 'Going Deeper than Microscopy: The Optical Imaging Frontier in Biology', Nature Methods, vol. 7, No. 8, 2010.

(56) References Cited

OTHER PUBLICATIONS

Office Action dated Jan. 14, 2014 for U.S. Appl. No. 13/055,552.
Office Action dated Jan. 29, 2014 for U.S. Appl. No. 12/867,265.
Sugiyama et al., 'Character Pattern Recognition Utilizing Independent Component', Proceedings of the 44th Conference of the Institute of Systems, Control and Information Engineers (ISCIE), p. 457-458, English abstract, 2000.
Taruttis et al., 'Motion Clustering for Deblurring Multispectral Optoaxoustic Tomography Images of the Mouse Heart', Journal of Biopmedical Optics, vol. 17, No. 1, pp. 16009-1 to 16009-4, Jan. 2012.
Taruttis et al., 'Imaging the Small Animal Cardiovascular System in Real-Time with Multispectral Optoacoustic Tomography', Proc of SPIE, vol. 7899, pp. 789913-1 to 789913-8, 2011.
Buehler et al., 'Video Rate Optoacoustic Tomography of Mouse Kidney Perfusion', Optics Letters, vol. 35, No. 14, pp. 2475-2477, Jul. 15, 2010.
Glatz et al., 'Blind Source Unmixing in Multi-Spectral Optoacoustic Tomography', Optics Express, vol. 19, No. 4, pp. 3175-3184, Feb. 14, 2011.
Morscher et al., 'Spectral Unmixing Using Component Analysis in Multispectral Optoacoustic Tomography', Proc SPIE, vol. 8089, 2011.
Morscher et al., 'Blind Spectral Unmixing to Identify Molecular Signatures of Absorbers in Multispectral Optoacoustic Tomography', Proc SPIE, Photons Plus Ultrasound: Imaging and Sensing, vol. 7899, 2011.
Office Action dated Jul. 31, 2014 for U.S. Appl. No. 13/386,491.
Ku et al., 'Thermoacoustic and Photoacoustic Tomography of Thick Biologial Tissues Toward Breast Imaging', Technogy in Cancer Research & Treatment, ISSN 1533-0346, vol. 4, No. 5, dated Oct. 2005.
Final Office Action dated Feb. 19, 2016 for U.S. Appl. No. 14/102,250.
Final Office Action dated Mar. 9, 2016 for U.S. Appl. No. 13/386,491.
Non-Final Office Action dated Dec. 3, 2015 for U.S. Appl. No. 14/141,773.
Office Action dated Mar. 11, 2016 for U.S. Appl. No. 13/055,552.
Xu et al., 'Time-Domain Reconstruction for Thermoacoustic Tomography in a Spherical Geometry', IEEE Transactions on Medical Imaging vol. 21, No. 7, pp. 814-822, Jul. 2002.
Erpelding et al., 'Three-Dimensional Photoacoustic Imaging with a Clinical Two-Dimensional Matrix Ultrasound Transducer', Photons Plus Ultrasound: Imaging and Sensing, Proc of SPIE, vol. 7899, 2011.
Office Action dated Jan. 28, 2014 for U.S. Appl. No. 13/386,491.
Office Action dated May 7, 2015 for U.S. Appl. No. 13/381,207.
Office Action dated Jul. 7, 2015 for U.S. Appl. No. 13/386,491.
Office Action dated Jul. 14, 2015 for U.S. Appl. No. 14/102,250.
Office Action dated Jul. 30, 2015 for U.S. Appl. No. 13/055,552.
Office Action dated Aug. 30, 2012 for U.S. Appl. No. 12/684,816.
Office Action dated Oct. 2, 2015 for U.S. Appl. No. 12/867,265.
Philips. White Pate for iU22 with X7-2 Probe, 2010, 1 pg, internet https://web/archive.org/web/20100908015304/http://healthcare.philips.com/main/products/ultrasound/transducers/7x_2.wpd.

Pratt, 'Image Sampling and Reconstruction,' Digital Image Processing: PIKS Scientific Inside by William K. Pratt, pub. Wiley-Interscience; 4 Edition (Feb. 9, 2007); ISBN: 0471767778; Chapter 4.
Razansky et al., 'Hybrid Photoacoustic Fluorescence Molecular Tomography Using Finite-Element-Based Inversion', Med Phis, vol. 34 No. 11, pp. 4293-4301, Nov. 2007.
Sugiyama et al., 'character pattern Recognition Utilizing Independent Component', Proceeding of the 44th Conference of the Institute of Systems, Control and Information Engineers (ISCIE), pp. 457-458, English abstract, 2000.
Taruttis et al., 'Motion Clustering for Deblurring Multispectral Optoacoustic Tomography Images of the Mouse Heart', Journal of Biomedical Optics, vol. 17 No. 1, pp. 16009.1-16009.4, Jan. 2012.
Yin et al., 'Tomographic Imaging of Absolute Optical Absorption Coefficient in Turbid Media Using combined Photoacoustic and Diffusing Light Measurements', Optics Letters, vol. 32 No. 17, pp. 2556-2558, 2007.
U.S. Appl. No. 12/867,265, Final Office Action, dated Dec. 16, 2016, 44 pages.
U.S. Appl. No. 13/386,491, Non-Final Office Action, dated Sep. 23, 2016, 54 pages.
U.S. Appl. No. 14/141,773, Notice of Allowance, dated Oct. 25, 2016, 21 pages.
U.S. Appl. No. 13/055,552, Notice of Allowance, dated Nov. 18, 2016.
U.S. Appl. No. 14/141,773, Final Office Action, dated Jun. 9, 2016, 49 pages.
Office Action dated Nov. 6, 2017 for U.S. Appl. No. 14/102,250.
Clement, et al.,A Hemisphere Array for Non-Invasive Ultrasound Brain Therapy and Surgery, Phys. Med. Biol. 45 ,2000 ,3707-3719.
Office Action dated Apr. 12, 2017 for U.S. Appl. No. 13/386,491.
U.S. Appl. No. 14/102,250, et al., Non-Final Office Action ,dated Mar. 13, 2017 ,42 pages.
Andreev,V.G. et al.,Inverse radon transformation for optoacoustic imaging, Biomedical Optoacoustics II, 4618 ,2002 ,pp. 137-145.
European Search Report dated Dec. 17, 2018 for EP10915P785EP.
Office Action dated Mar. 15, 2019 for U.S. Appl. No. 14/102,250.
Andreev, et al., Image Reconstruction in 3D Optoacoustic Tomography System with Hemispherical Transducer Array, Biomedical Optoacoustics III, SPIE vol. 4618 ,2002.
Wang, et al., Photoacoustic Tomography System for Noninvasive Real-Time Three-Dimensional Imaging of Epilepsy, Biomedical Optics Express, vol. 3 No. 6 ,Jun. 1, 2012.
Chaudhary, et al.,Comparison of Reconstruction Algorithms for Sparse-Array Detection Photoacoustic Tomography, SPIE Bios, vol. 7564 ,Feb. 23, 2010.
Roumeliotis, et al.,Singular Value Decomposition Analysis of a Photoacoustic Imaging System and 3D Imaging at 0.7 FPS, Optics Express, vol. 19 No. 14 ,Jun. 27, 2011
Notice of Allowance dated Mar. 25, 2019 for U.S. Appl. No. 13/386,491.
Office Action dated Aug. 13, 2019 for U.S. Appl. No. 14/102,250.

\* cited by examiner

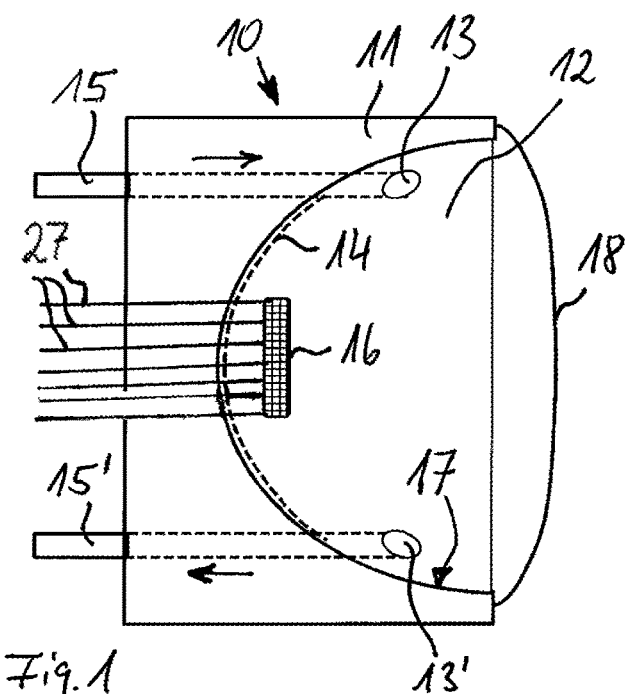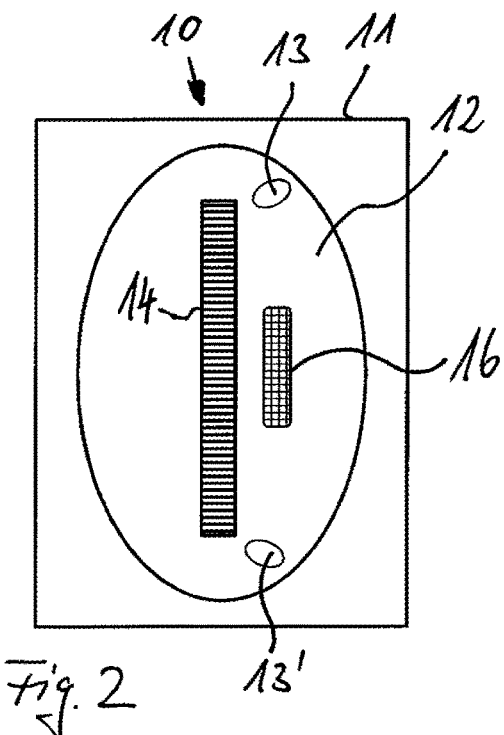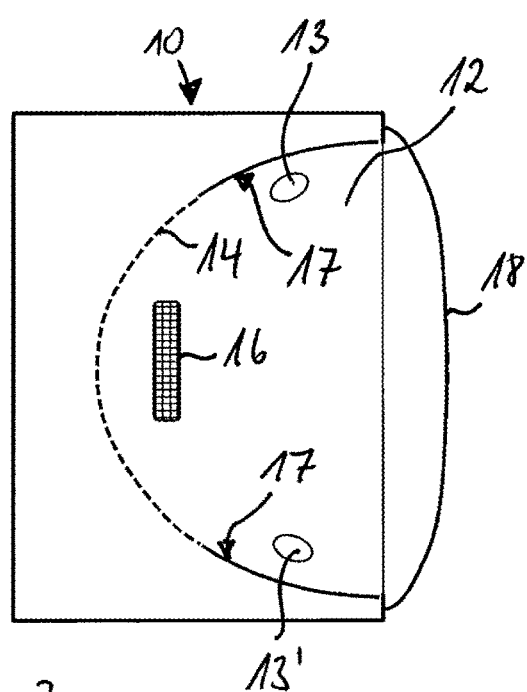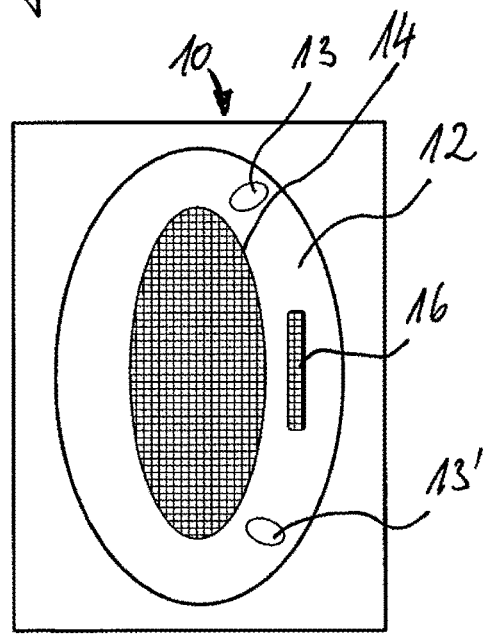

HANDHELD DEVICE AND METHOD FOR TOMOGRAPHIC OPTOACOUSTIC IMAGING OF AN OBJECT

RELATED APPLICATIONS

This application claims priority to U.S. Provisional Application No. 61/735,578 filed on Dec. 11, 2012 and to European Patent Application 12 008 270.6, filed on Dec. 11, 2012, both of which are hereby incorporated by reference in their entireties.

TECHNICAL FIELD

The present disclosure relates to a handheld device and method for optoacoustic imaging of an object.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 1 shows a cross-sectional side view of a first embodiment of the handheld device according to the present disclosure.

FIG. 2 shows a front view of the first embodiment of the handheld device.

FIG. 3 shows a cross-sectional side view of a second embodiment of the handheld device according to the present disclosure.

FIG. 4 shows a front view of a third embodiment of the handheld device according to the present disclosure.

DETAILED DESCRIPTION

Figure 5:
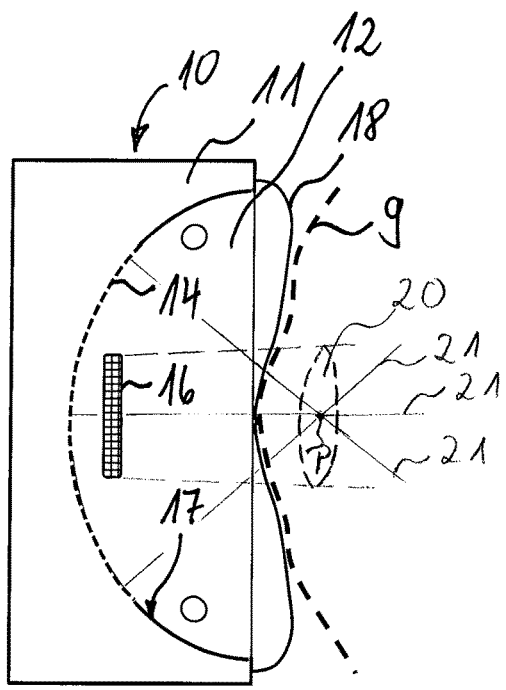
FIG. 5 shows a cross-sectional side view of a fourth embodiment of the handheld device according to the present disclosure.

Optoacoustic imaging is based on the photoacoustic effect, according to which ultrasonic waves are generated due to an absorption of electromagnetic radiation by an object, e.g. a biological tissue, and a subsequent thermoelastic expansion of the object.

Optoacoustic imaging of biological tissues provides a unique combination of high spatial resolution and rich contrast based on spectrally-dependent absorption of light. Techniques like multispectral optoacoustic tomography (MSOT) are therefore able to simultaneously render images of anatomical, functional and molecular contrast by exciting tissues at several optical wavelengths, thereby enabling highly promising applications in molecular imaging and diagnostics, drug development and treatment monitoring.

United States Patent Application Publication No. 2008/0071172 A1 discloses an apparatus combining pulse-echo ultrasound imaging with optoacoustic imaging comprising a conventional linear ultrasound probe and an attachment thereto, wherein said attachment comprises an illumination assembly used to excite optoacoustic signals in the object and, optionally, an additional set of ultrasound detection elements arranged for detection of optoacoustically-induced signals. While the general goal of said apparatus is a combination of pulse-echo ultrasound and optoacoustic imaging, it cannot be ensured that high-quality optoacoustic images, in particular with a high signal-to-noise ratio, quantification and spatial resolution, are obtained from regions of interest on or within the object.

In some embodiments the present disclosure relates to providing a handheld device and a corresponding method allowing for an improved and reliable optoacoustic imaging of an object, for example, allowing for an acquisition of high-quality optoacoustic images, exhibiting, for example, high signal-to-noise ratio, from regions of interest on or within the object in a simple and reliable manner.

An embodiment of the handheld device for optoacoustic imaging of an object according to the present disclosure comprises an irradiation unit for irradiating the object with electromagnetic radiation, for example, light, and a detector unit for detecting acoustic waves, for example ultrasonic waves, which are generated in the object upon irradiation with electromagnetic radiation, wherein the detector unit comprises an array of detector elements. The handheld device further comprises a recess in which the irradiation unit and the array of detector elements are provided, wherein the detector elements are arranged in the recess, such that the surface normal of at least a part of the detector elements is directed to a region of interest on or within the object.

In an embodiment of a method for optoacoustic imaging of an object according to the present disclosure the object is irradiated with electromagnetic radiation, for example, light, by means of an irradiation unit and acoustic waves, for example, ultrasonic waves, are generated in the object upon irradiation with electromagnetic radiation and detected by means of an array of detector elements, wherein the irradiation unit and the array of detector elements are provided in a recess, wherein the detector elements are arranged in the recess such that the surface normal of at least a part of the detector elements is directed to a region of interest on or within the object.

The term "handheld device" within the meaning of the present disclosure relates to any optoacoustic imaging device which is adapted for being seized and held by clasping with fingers and/or a hand in order to position the handheld device onto an object under investigation and/or to move the handheld device by hand relative to the object under investigation, for example, by positioning it onto or moving it along an exterior surface of the object, e.g. the skin of a patient. The term "handheld device" also relates to optoacoustic imaging devices in which only a component thereof, such as a handheld probe comprising the irradiation unit and/or the detector unit, is configured for being seized and held by clasping with fingers and/or a hand for same purposes. In some embodiments, the size of a handheld device or a respective handheld probe within the meaning of the present disclosure is less than 15 cm in width and/or depth and/or height. The term "handheld device" further relates to any optoacoustic imaging device which is designed for acquiring tomographic optoacoustic images at arbitrary orientations of the handheld device or handheld probe, respectively. For example, when acquiring images from the object, the orientation of the handheld device or probe can vary from a vertical up to a vertical down orientation including all orientations in between, for example, a horizontal orientation.

The present disclosure is based on the approach to provide a handheld optoacoustic imaging device with a recess in which both an irradiation unit and a detector unit are arranged, wherein the detector unit may comprise a curved array of ultrasound transducers, i.e. detector elements, and wherein at least one of the following elements or parameters of the handheld device are designed or chosen such that high-quality optoacoustic images from the region of interest on or within the object can be acquired in a simple and reliable manner: the shape of the recess, the positioning of the recess relative to the object, the arrangement of the irradiation unit within the recess, the shape of the array of detector elements, the arrangement of the array of detector elements within the recess and/or the direction of a surface normal of at least a part of the detector elements. In some instances, the direction of the surface normal of the detector elements, which corresponds to the direction along which the detector elements have the highest sensitivity for ultrasound waves, is directed to the region of interest on or within the object. In some embodiments, the surface normal of the detector elements intersect in an intersection point or in an intersection region which is located in the region of interest from which images are to be acquired. Moreover, the irradiation unit is arranged in the recess and designed such that a region on or within the object which is irradiated with the electromagnetic radiation coincides or overlaps with the region of interest and/or the intersection point or intersection region of the normal of the detector elements. By this means, it can be ensured that images with an improved signal-to-noise-ratio can be acquired from different depths within the object.

The present disclosure thus relates to acquiring high-quality optoacoustic images of an object by means of a handheld device of an overall simple yet efficient design.

The present disclosure further relates to a handheld device for sectional optoacoustic imaging of soft tissues for clinical imaging applications. The device uses the principles of multispectral optoacoustic tomography, i.e. illumination of the imaged object with light, in some instances, at multiple wavelengths, with a subsequent detection of the generated high frequency ultrasonic (photoacoustic) responses. In some embodiments, an imaging device employing the photoacoustic effect comprises a laser and a detection system. The laser radiation is delivered into the imaged region while the absorbed light is converted into heat and creates thermoelastic expansion, i.e. a propagating acoustic (ultrasonic) wave. Detection of such acoustic signals allows for spatial localization of absorbers. If detection is performed by multiple detectors arranged around the imaged object, a tomographic reconstruction of the scanned object becomes possible. Such an imaging modality thus delivers images of tissue anatomy based on light absorption coefficients. In contrast to pure ultrasound scanners, whose contrast capability derives from acoustic properties of the matter, optoacoustic modalities provide information about the optical absorption of a tissue depending on the color of the light excitation. A sequential exposure of the tissue to a wavelength-variable source allows for spectral decomposition of the reconstructed images. This mode of operation extends the palette of applications to spatially-resolved imaging of functional tissue parameters, such as blood oxygenation, as well as quantification of intrinsic biomarkers and extrinsically-administered contrast agents.

The light penetrating the tissue is affected by scattering and absorption. These effects may strongly affect photoacoustic signal generation and, thus, a suitable system for the delivery of the excitation light may be a part of an optoacoustic imaging system. At the same time, the imaging apparatus may be configured to provide acoustic coupling for efficient and sensitive ultrasound detection.

The present disclosure relates to a novel design of a handheld tomographic optoacoustic probe as well as a corresponding method for tomographic optoacoustic imaging. Certain embodiments are designed in a way that the region of illumination overlaps with the ultrasound-detection field of view resulting in better contrast of the image. In addition, in some embodiments, a liquid chamber is provided for optical and acoustic coupling, while suppressing out-of-imaging-plane waves that are the main cause of image artifacts.

In some embodiments, the handheld device comprises a container in which the recess together with the irradiation unit and the detector unit are provided and a carrier on which or in which the container is moveably mounted such that, for example, while images are acquired from the object, the container can be moved towards the object and/or away from the object, wherein the location of the region of interest, for example, the intersection point or intersection region of the normal of the detector elements, and/or the irradiated region of the object can be changed. By this means, high-quality optoacoustic tomographic images can be acquired from different regions at different depths on or within the object without the requirement of moving the handheld device itself relative to the object. The latter facilitates the handling of the handheld device while the image capturing process considerably.

In a further embodiment, the recess is provided, and may be sealed, with a cover element such that the recess together with the cover element constitute a cavity and wherein the cavity accommodates a coupling medium, for example, water. In this embodiment, the recess forms a first part and the cover element forms a second part of a closed cavity, which is filled with the coupling medium, having an acoustic impedance such that reflections of acoustic waves emanating from the object, passing through the cover element and incident upon the detector elements are minimized or eliminated. It is also contemplated that the coupling medium may have a refractive index such that reflections of electromagnetic radiation emerging from the irradiation unit into the recess, passing through the cover element and entering into the object are minimized or eliminated. In some instances, the acoustic impedance and/or the refractive index of the coupling medium is identical or close to the acoustic impedance and/or the refractive index of the object. In such embodiments, the recess in which the irradiation unit and the detector unit are integrated also constitutes a container for accommodating the coupling medium. This embodiment represents a very compact design of the handheld device which is, therefore, of particular advantage in handheld applications in which high-quality optoacoustic images are obtained.

In some embodiments, the region of interest of the object, such as the intersection point or intersection region of the normal of the detector elements, is located around the cover element or beyond the cover element. Alternatively or additionally, the irradiated region of the object is located around the cover element or beyond the cover element. By means of this embodiment, high-quality tomographic images from the surface of the object or within the object can be obtained in a simple and reliable way.

In some instances, the cover element is arranged and/or designed such that at least a section of the cover element comes into contact with the object while images are acquired from the object. That is, when optoacoustic images are acquired, the handheld device is placed onto the object under investigation such that the cover element comes into contact with the surface of the object under investigation.

In some embodiments, the cover element is a mechanically flexible element, such as a membrane or a film. Due to its flexibility, the shape of the cover element can be easily adapted to the surface of the object under investigation. By this means, a close contact between the distal end of the handheld device and the object can be achieved which ensures a good optical and acoustical coupling between the irradiation unit and detector unit on the one hand and the object on the other hand. This further ensures the acquisition of high-quality images.

In some embodiments, at least a section of the cover element has a convex shape, such as a cushion-like shape. In some embodiments when the cover element is mechanically flexible and the cavity is filled with the coupling medium, the cover element exhibits a cushion-like behavior by means of which it easily adapts to various surface topologies of objects under investigation in a particularly reliable way. The above-mentioned advantages apply according.

According to a further embodiment of the present disclosure, at least one conveyance unit is provided for conveying the coupling medium into and/or out of the recess. The conveyance unit may comprise tubes or pipes which are connected over a pump to a reservoir, which is filled with the coupling medium. In some instances, by continuously circulating the coupling medium, i.e. removing medium from the recess and conveying medium from the reservoir into the recess, gas bubbles evolving in the coupling medium in the recess are efficiently removed therefrom. As a result, adverse effects of gas bubbles on the detection of the acoustic waves, such as acoustic scattering, attenuation and reflections, can be efficiently avoided so that a high image quality can be ensured in a simple and efficient way.

In a further embodiment, the array of detector elements is a curved array of detector elements or a two-dimensional array of detector elements. In the case of a curved array, the detector elements are arranged along an arc or bow, such as in a circular arc, wherein the surface normal of the detector elements of the array intersect in the center of the curvature of the arc or circle, respectively. By this means, the detector elements efficiently collect acoustic waves from a region upon or within the object, which is located around the center of the curvature. If, for example, the detector elements are arranged along a curved two-dimensional surface which is spherically shaped, such as a concave surface and/or a calotte, the detector elements collect acoustic waves from a region of the object located around the center of a sphere.

In some embodiments, the recess comprises and/or is constituted by at least one curved, for example, a concave, surface. Additionally or alternatively, the curved array of detector elements is provided at the curved surface of the recess and/or constitutes a section of the curved surface of the recess. Additionally or alternatively, the irradiation unit is provided at the curved surface of the recess. By one or more of these measures, a very compact design of the handheld device is achieved without negatively affecting the quality of optoacoustic images acquired with the device.

According to a further embodiment, at least a section of the curved surface of the recess is designed, for example, shaped, such that a reflection of acoustic waves incident on the curved surface of the recess towards the array of detector elements is reduced or avoided. By this means it is ensured that only direct acoustic waves directly emanating from the object are detected by the detector elements, whereas a detection of indirect acoustic waves which are reflected at the surface of the recess is efficiently reduced or eliminated.

In further embodiments of the present disclosure, the shape, for example, the curvature, and/or the size and/or the angular coverage of the array of detector elements depend on the size of the object and/or the region of interest of the object. In this manner it is ensured that for any kind of objects, e.g. large areas of the human body or small tissue specimen, acoustic waves are detected by the array of detector elements in the broadest possible solid angle range around the imaged region of the object. By means of the shape of the array of detector elements the orientation of individual detector elements toward the imaged region can be optimized and/or the distance of the detector elements from said region can be minimized in order to increase the detected optoacoustic responses, i.e. the acoustic waves, of the detector elements and minimize effects of acoustic refractions and surface mismatches.

It will be readily understood by one of skill in the art having the benefit of this disclosure that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

FIG. 1 shows a cross-sectional side view of a first embodiment of the handheld device 10 according to the present disclosure. The handheld device 10 comprises a container 11 in which a recess 12 having a surface 17 is provided. The container 11 is made of a metal in some embodiments. The recess 12 in the container 11 has the shape of a part of a sphere, such as of a calotte, or a part of an ellipsoid.

In the recess 12 an array of ultrasound detector elements 14 is provided. In the given example, the detector elements of the array 14 are arranged on or along the surface 17 of the recess 12. As shown in the figure, the array is provided in a region of the bottom of the recess 12. In some instances, the array 14 of detector elements is a linear array.

The recess 12 has an aperture in which an end face of a fiber bundle 16 is provided. The end face of the fiber bundle 16 comprises a plurality of end faces of individual fibers 27 of the fiber bundle, whereof only a few fibers 27 are indicated in FIG. 1. The fibers 27 are connected with a light source (not shown), such as a laser.

In the recess 12 two openings 13 and 13' are provided through which a liquid, such as an acoustic and/or optical coupling medium, can be filled into the recess 12 and/or sucked off the recess 12. The liquid is conveyed to and from the openings 13 and 13', respectively, by means of conveyance means 15 and 15', like tubes or channels. In some embodiments, the coupling medium is conveyed from a reservoir (not shown) via a first conveyance means 15 (see arrow rightwards) and a first opening 13 into the recess 12, while coupling medium accommodated in the recess 12 is simultaneously sucked off the recess 12 via a second opening 13' and a second conveyance means 15' (see arrow leftwards) and, in some instances, conveyed back to the reservoir. In this manner, a continuous circulation of coupling medium is achieved by means of which bubbles generated in the coupling medium accommodated in the recess 12 can be efficiently removed.

At the open end of the recess 12 the container 11 is provided with a flexible membrane 18 such that the recess 12 is sealed in a gas-tight and/or liquid-tight manner and a closed cavity accommodating the coupling medium is obtained. Due to the coupling medium filling of the cavity and the flexibility of the membrane 18 the latter exhibits a slightly curved, for example, convex, shape as indicated in FIG. 1.

FIG. 2 shows a front view of the first embodiment of the handheld device 10 according to the present disclosure. For sake of clarity, the membrane 18 (see FIG. 1) is not shown in FIG. 2.

As shown by the oval shape of the recess 12 in this view together with the circular shape in the side view of FIG. 1, the recess 12 of the first embodiment has the form of a part of an ellipse or an ellipse-like body. As also shown in FIG. 2, the array 14 of detector elements is a linear array of, e.g. 128 or 256, individual detector elements arrayed along a line.

The end face of the fiber bundle 16 is arranged in the recess 12 with a certain lateral offset from the array 14 of detector elements. Same applies for the openings 13 and 13' through which coupling medium is guided to and from the recess 12, respectively.

FIG. 3 shows a cross-sectional side view of a second embodiment of the handheld device 10 according to the present disclosure. Unlike the first embodiment shown in FIGS. 1 and 2, the detector elements of the array 14 are not arranged on the surface 17 of the recess 12, but the array 14 of detector elements forms a part of the surface 17 of the recess 12. This is achieved in some embodiments, by providing the surface 17 of the recess 12 with a further recess in which the array 14 is integrated. In some instances, the surface of the plurality of detector elements of the array 14 aligns with the surface 17 of the recess 12, as indicated in FIG. 3. In this embodiment, the array 14 constitutes a part of the surface 17 of the recess 12.

With respect to the end face of the fiber bundle 16, the openings 13 and 13', the conveyance means (not shown), as well as the membrane 18 and the coupling medium filling of the cavity, the elucidations given with respect to FIGS. 1 and 2 apply accordingly.

FIG. 4 shows a front view of a third embodiment of the handheld device 10 according to the present disclosure. In this embodiment, the array 14 of detector elements is a curved two-dimensional array of detector elements, wherein a plurality of detector elements are arranged along a curved surface the contour thereof may have the form of, e.g., an ellipse.

Like in the first and second embodiment shown in FIGS. 1 to 3, the detector elements of the two-dimensional array in the third embodiment shown in FIG. 4 can be arranged on or along the surface 17 of the recess 12 or can be integrated into or constitute a part of the surface 17 of the recess 12. Apart from that, the elucidations given with respect to FIGS. 1 to 3 apply accordingly.

FIG. 5 shows a cross-sectional side view of a fourth embodiment of the handheld device 10 according to the present disclosure.

Also in this embodiment, the array 14 of detector elements is arranged in a region of the bottom of and integrated in the surface 17 of the recess 12 in the container 11, wherein the detector elements of the array 14 are in alignment with the run of the surface 17. The depth of the recess 12 in this embodiment is less than the depth of the recesses of the embodiments shown in FIGS. 1 and 3. Apart from that, the elucidations given in relation to FIGS. 1 to 4 apply accordingly.

The distal end of the handheld device 10 is in contact with a curved surface 9 of an object under investigation. Because of the mechanical flexibility of the membrane 18, which seals the coupling medium-filled recess 12 of the container 11, the membrane 18 easily adapts itself to the shape of the surface 9 of the object. In this way, it is ensured that the handheld device 10 can be positioned on the object under investigation very stably.

In some embodiments, the sensitivity of the detector elements of the array 14 for ultrasonic waves is focused to a focus point or a focus region which defines the region of interest from which images of the object are acquired. In the given embodiment, the surface normals 21 of each of the detector elements of the array 14 intersect at an intersection point P. For sake of clarity, only three surface normals 21 are shown in the present figure. It is not necessary that all the surface normals 21 have to intersect at an intersection point P in order to define a region of interest within the object. The surface normals 21 of the detector elements of the array may simply be directed to the region of interest in embodiments within the scope of this disclosure.

In the shown embodiment, the light emitted from the end face of the fiber bundle 16 has the form of a flat cone 20 the boundaries of which are indicated by dashed lines. In some embodiments, the intersection point P of the surface normals 21 of the detector elements of the array 14 comes within the light cone 20 emerging form the light bundle 16 and incident onto the surface 9 of the object.

As already mentioned above, by means of the flexible membrane 18 the handheld device 10 can be positioned on the object under investigation very stably. Moreover, the membrane 18 allows for easily moving the handheld device 10 relative to the object, i.e. along the surface 9 of the object and/or towards or away from the surface 9 of the object. Therefore, by means of moving the handheld device 10 along the surface 9 of the object and/or towards or away from the surface 9 of the object, the region of interest on or within the object, which is defined by the direction of the surface normals 21 of the detector elements and/or the cone 20 of the light emitted from the light bundle 16, can be defined easily and reliably.

Additionally or alternatively, the region of interest on or within the object, from which images of the object shall be acquired, can be defined by varying the distance of the array 14 of detector elements and/or the distance from the end face of the fiber bundle 16 from the surface 9 of the object under investigation.

Figure 6:
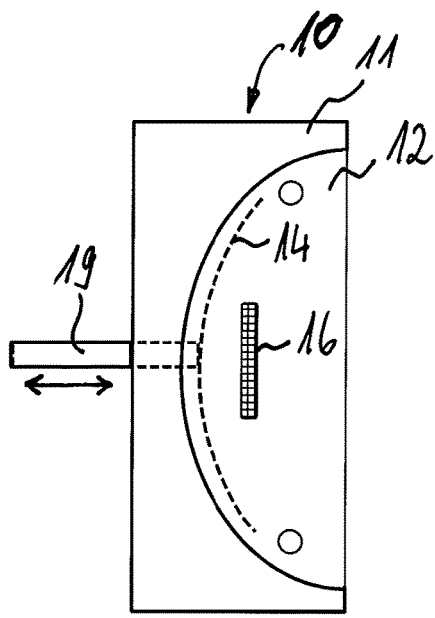
FIG. 6 shows a cross-sectional side view of a fifth embodiment of the handheld device according to the present disclosure.

FIG. 6 shows a cross-sectional side view of a fifth embodiment of the handheld device 10 according to the present disclosure by means of which the region of interest on or within the object can be varied by changing the distance of the array 14 of detector elements from the object.

For this purpose, the array 14 is moveably mounted in the recess 12. In some instances, a moving mechanism 19 is provided by means of which the array 14 can be moved back and forth, i.e. away from or towards the object (see double-arrow). In the representation of FIG. 6, the moving mechanism 19 is schematically represented by a single rod which is moveably mounted in a guide provided in the container 11. Of course, further and even more complex moving mechanisms 19 can be provided for realizing a back-and-forth movement of the array 14.

Additionally or alternatively, also the end face of the fiber bundle 16 can be moveably mounted in the recess 12 such that the cone 20 of the light emerging from the end face of the fiber bundle 16 can be moved towards and/or away from the object.

Regarding the remaining components and features of the handheld device 10, for example, with respect to the membrane 18, the conveyance means, the intersection point P and the light cone 20, the elucidations given above with respect to the embodiments given in FIGS. 1 to 5 apply accordingly.

Figure 7:
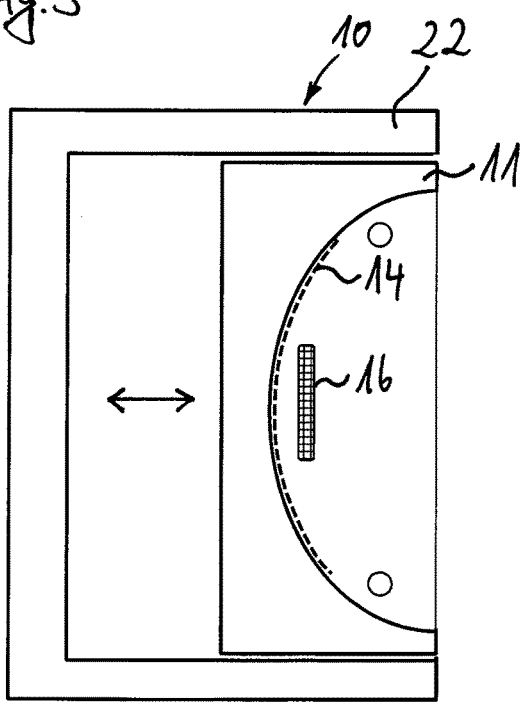
FIG. 7 shows a cross-sectional side view of a sixth embodiment of the handheld device according to the present disclosure.
Figure 8:
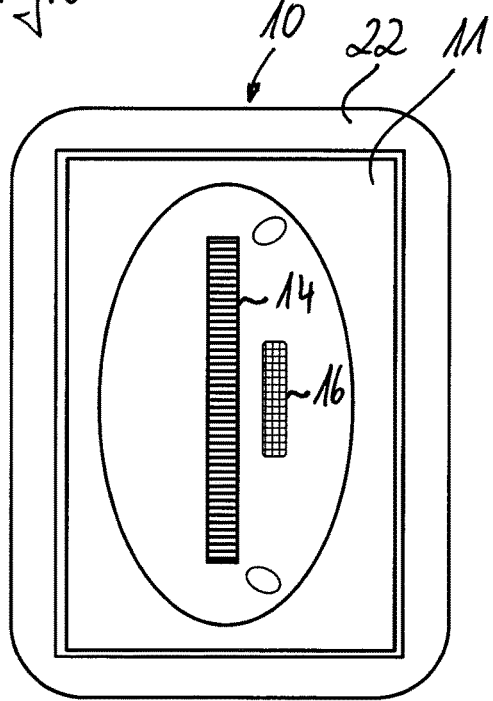
FIG. 8 shows a front view of the sixth embodiment of the handheld device according to the present disclosure.

FIG. 7 shows a cross-sectional side view of a sixth embodiment of the handheld device 10 according to the present disclosure by means of which the region of interest on or within the object can be varied by changing the distance of the array 14 of detector elements and the end face of the fiber bundle 16 from the object. For this purpose, a carrier 22 is provided in which the container 11 is moveably, for example, slidably, mounted such that it can be moved by a respective moving mechanism (not shown) back and forth (see double-arrow). FIG. 8 shows a corresponding front view of the sixth embodiment of the present disclosure. As obvious for the figure, the carrier 22 surrounds the container 11 such that the handheld device 10 can be easily grasped by the hand of a person without limiting the back-and-forth movement of the container 11. Regarding the remaining components and features of the handheld device 10, for example, with respect to the membrane 18, the conveyance means, the intersection point P and the light cone 20, the elucidations given above with respect to the embodiments given in FIGS. 1 to 6 apply accordingly.

Figure 9:
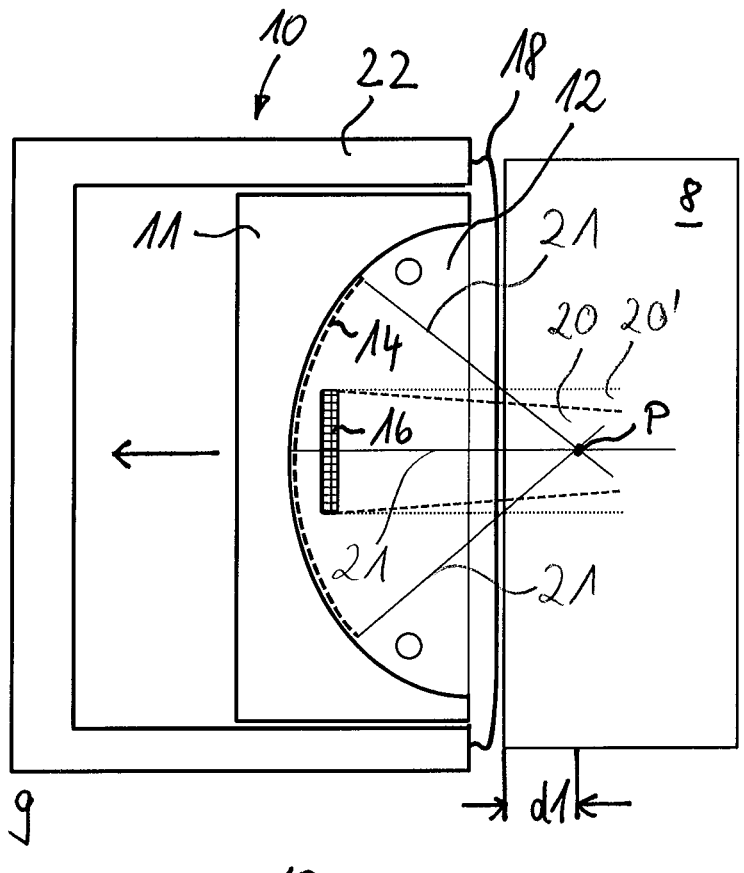
FIG. 9 shows a cross-sectional side view of the sixth embodiment of the handheld device according to the present disclosure in a first operational status.

FIG. 9 shows a cross-sectional side view of the sixth embodiment of the handheld device 10 according to the present disclosure in a first operational status in which the movably mounted container 11 is in a first position with respect to the carrier 22 and the object 8. According to the embodiment shown in FIG. 5, the surface normals 21 of the detector elements of the linear of two-dimensional array 14 intersect at an intersection point P located beyond membrane 18 at a first depth d1 within the object 8. The intersection point P is located in a center of curvature of the array 14 of the detector elements. If, e.g., the array 14 is spherically shaped then the intersection point P is located in the center of a sphere.

Moreover, the intersection point P lies within the illuminated area of the object 8, i.e. within the cone 20 of the light beam emerging from the end face of the fiber bundle 16. In the example shown, the cone 20 is a slightly converging light beam. Alternatively, any other kind of light beams is possible, e.g. a pencil-like parallel light beam 20' or a slightly diverging cone like the one shown in FIG. 5.

By moving the container 11 away (see arrow) from the object 8, the intersection point P as well as the cone 20 or 20', respectively, are moved within the object 8 to a second depth d2 within the object 8, wherein the second depth d2 is smaller than the first depth d1. This is illustrated by means of FIG. 10 which shows a cross-sectional side view of the sixth embodiment of the handheld device 10 according to the present disclosure in a second operational status. Regarding the remaining components and features of this embodiment of the handheld device 10, the elucidations given above with respect to the embodiments given in FIGS. 1 to 9 apply accordingly.

Figure 10:
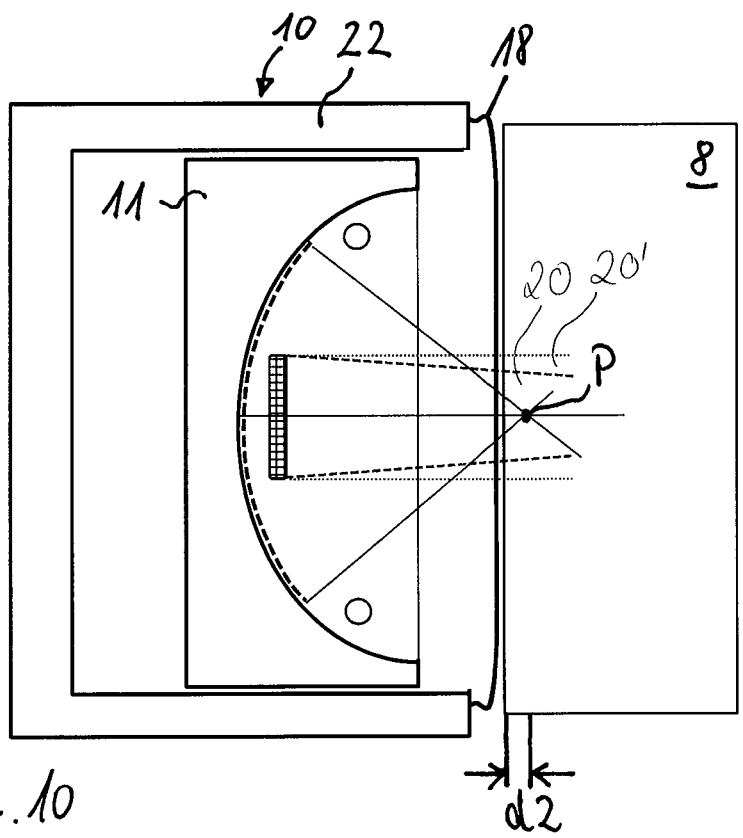
FIG. 10 shows a cross-sectional side view of the sixth embodiment of the handheld device according to the present disclosure in a second operational status.

In the embodiment shown in FIGS. 9 and 10, the membrane 18 is provided at the carrier 22 and forms together with the recess 12 a cavity which is filled with coupling medium. Alternatively, like in the embodiments shown in FIGS. 1, 3 and 5, the membrane 18 can be affixed to the container 11 so that it moves together with the container 11 towards and/or away from the object 8.

Figure 11:
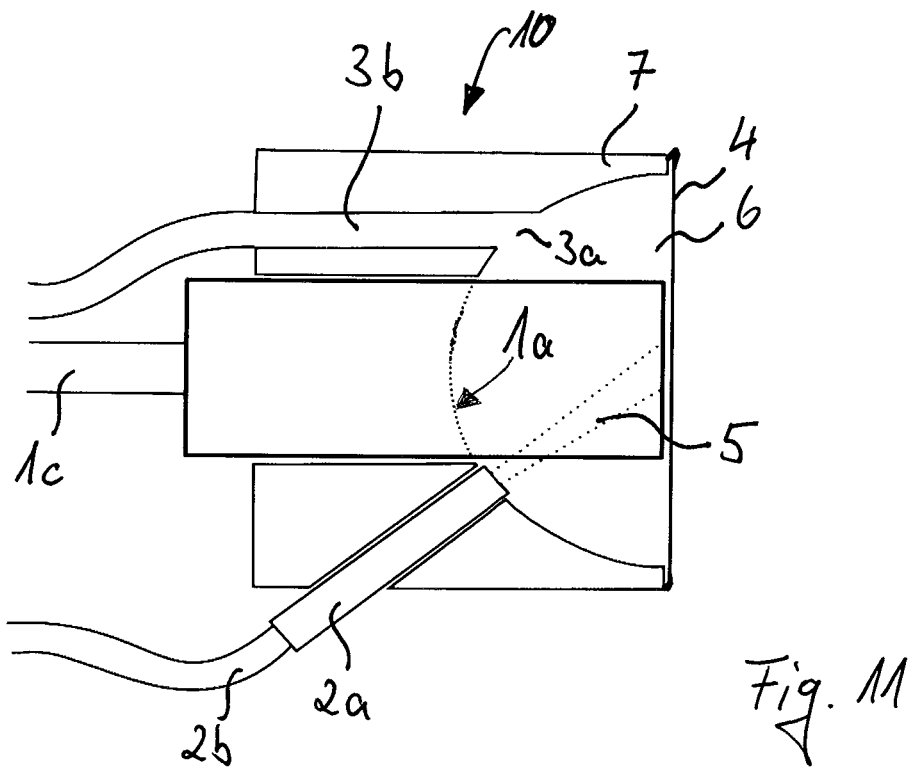
FIG. 11 shows a cross-sectional side view of an example of a first prototype of the handheld device according to the present disclosure.
Figure 12:
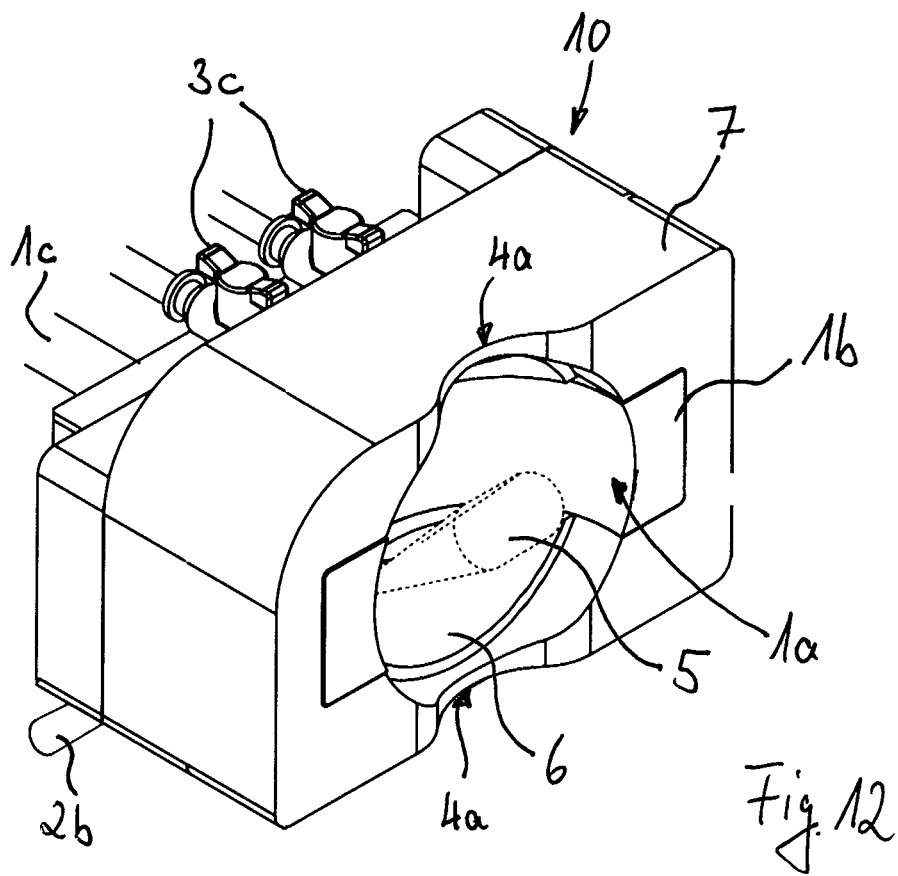
FIG. 12 shows a perspective view of the example of a first prototype of the handheld device according to the present disclosure.

FIG. 11 shows a cross-sectional side view of an example of a first prototype of the handheld device 10 according to the present disclosure. FIG. 12 shows a perspective view of the example of a first prototype of the handheld device 10 according to the present disclosure.

The device 10 comprises a high frequency cylindrically focused tomographic ultrasound transducer array 1a to 1c, fiber bundles 2a and 2b, a liquid-filling mechanism 3a to 3c, a coupling membrane 4, an encasement 7 and a recess 6 provided in the encasement 7.

The transducer array comprises a piezo-composite sensing surface 1a, a casing 1b for the transducer array and electric cables 1c connected with the individual transducers of the transducer array. The sensing surface 1a of the transducer array is provided in the recess 6 of the encasement 7. Each of the fiber bundles comprises a metal ferrule 2a and a fiber cable 2b containing multiple multi-mode fibers. The liquid-filling mechanism comprises channel outputs 3a of the chamber, wherein a first output is provided for delivering the liquid to the chamber and a second output is provided for removing the remaining gas, two channels 3b going through the chamber enclosure, and two pipe connectors and valves 3c.

Electromagnetic radiation, for example, light, emerges from the distal end of each of the fiber cables 2b in the form of a slightly flattened cone 5 which is running co-axially with the metal ferrule 2a. The cone 5 represents the light beam illuminating a tissue surface (not shown).

The device 10 is especially designed for a convenient access to different parts of the human body, most of them having a convex shape, e.g. especially limbs, torso or a neck.

The ultrasound array 1a to 1c comprising a plurality of cylindrically-focused detectors is assembled together with four optical waveguides 2a and 2b using the encasement 7 which is made of metal or plastics in some embodiments. The front face of the encasement 7, i.e. the distal end of the handheld device 10, is provided with a recess 6 in order to form a chamber which is filled with a liquid, for example, an acoustical and/or optical coupling medium, and which is sealed by the membrane 4 (not shown in FIG. 12 for reasons of clarity). The recess 6 together with the sealing membrane 4 forms a closed cavity which is filled with the coupling medium.

The membrane 4 is may be transparent for at least a part of the electromagnetic radiation, such as light, emerging from the fiber cables 2b. In some instances, the membrane 4 is acoustically-matched to the acoustical properties of the tissue.

The front aperture, i.e. open end of the recess 6 sealed with the membrane 4, of the handheld device 10 is designed to have contact with the tissue. The flexible, or alternatively rigid, membrane 4 is designed such that it can assume a concave shape, which is optimal for radial ultrasound wave propagation for a given arrangement of detectors. Different forms of the membrane 4 can be used within the assembly by exchanging the front frame of the encasement 7.

In the embodiment shown, the encasement 7 has an indentation 4a which is sealed with the flexible membrane 4 such that a section of the membrane 4 in the region of the indentation 4a exhibits an indentation. Due to the mechanical flexibility of the membrane 4, the form of the indentation of the membrane 4 follows the object surface's curvature. By this means, the object can be safely and reliably positioned in the indentation of the membrane and can be illuminated with the irradiation light cone 5.

The light delivery system comprises a fiber bundle consisting of 640 multimode fibers enclosed in four metal ferrules 2a. The fibers deliver illumination onto the tissue surface attached to the membrane. Diameters of core and two claddings of fiber used were 189, 1 and 200 microns, respectively.

The assembly of light guides 2a and 2b, the array of ultrasonic transducers 1a and the membrane 4 are fixed with the encasement in which a chamber for the index-matching liquid is formed. The mentioned liquid may have acoustic properties similar to the tissue under investigation. Moreover it is preferred that it does not absorb the excitation radiation.

In some embodiments, the recess 6 provided in the encasement 7 has a hemispherical shape. In some instances, its surface is polished in order to achieve good light reflection. In this way, electromagnetic radiation reflected from the tissue surface or the membrane 4 will be guided into the imaged region of interest so that higher illumination efficiency, better signal-to-noise ratio and therefore a better image quality will be achieved.

Figure 13:
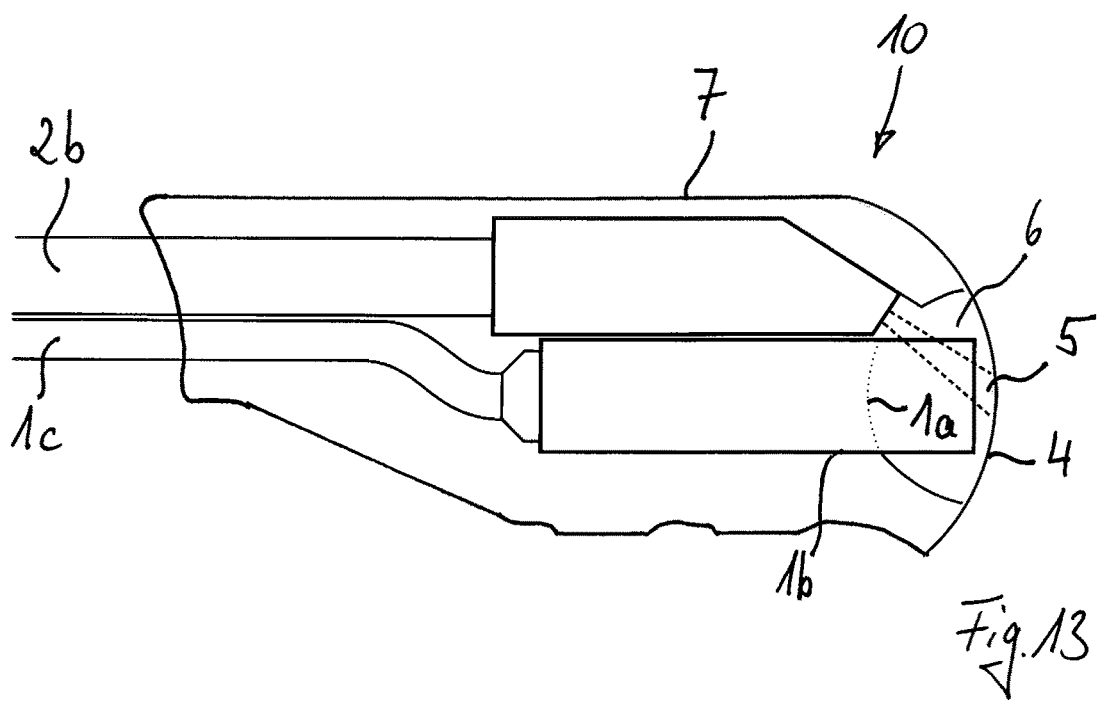
FIG. 13 shows a cross-sectional side view of an example of a second prototype of the handheld device according to the present disclosure.
Figure 14:
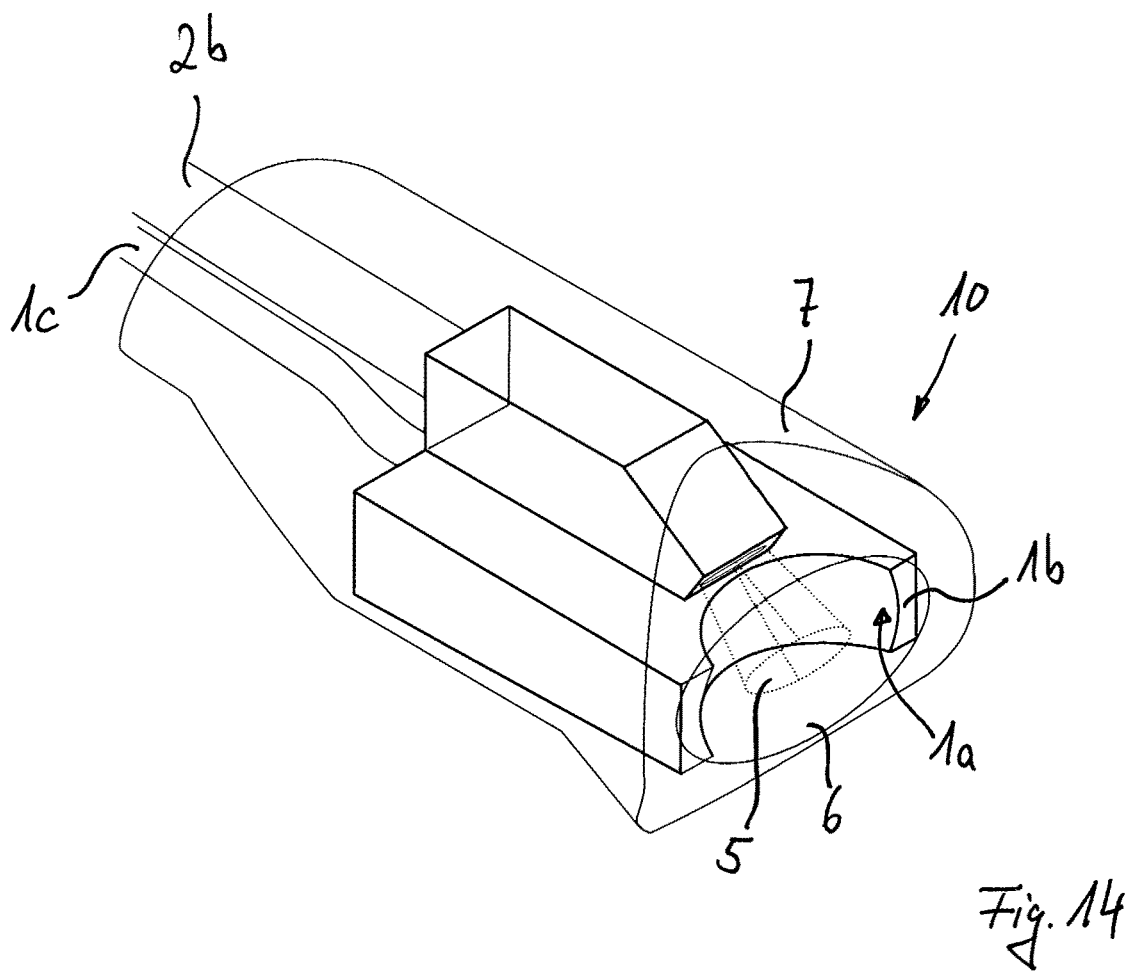
FIG. 14 shows a perspective view of the example of a second prototype of the handheld device according to the present disclosure.

FIG. 13 shows a cross-sectional side view of an example of a second prototype of the handheld device 10 according to the present disclosure. FIG. 14 shows a perspective view of the example of a second prototype of the handheld device 10 according to the present disclosure.

The, curved or two-dimensional, transducer array 1a and the optical fiber bundle 2b are stacked and encased within a two-piece metal casing 7. The array 1a consists of 128 transducer elements arrayed along an arc, such as a circular arc, and cylindrically focused to the center of the arc along which they are arranged, i.e. the surface normal (not shown) of each of the transducer elements intersect at the center of the arc or within a region around the center of the arc or curvature.

The fiber bundle 2b consists of 256 individual multimode fibers having a 283 µm diameter core and 300 µm diameter cladding. Fiber tips were bent by 33 degrees with respect to the normal to the face plane of the ferrule (not shown) and the transducer elements in order to direct the light beam 5 onto the imaged region of interest on or within the object.

The coupling membrane 4 between the liquid-filled recess 6 and the imaged object is made of a semi-rigid plastic in some embodiments. Its surface may be glued with pressure-sensitive adhesive onto the convex face of the casing 7.

The handheld device 10 shown in FIG. 14 may also comprise a liquid recirculator for removing liquid from the recess 6 and re-introducing liquid into the recess 6. According to the embodiments shown in FIGS. 1 to 12, respective openings in the recess 6 as well as appropriate conveyance means for conveying liquid, for example, coupling medium, into and out of the recess 6 would have to be provided.

Moreover, the embodiments described with reference to FIGS. 1 to 14 may be further equipped with a liquid temperature control unit for controlling the temperature of the liquid accommodated in the recess 6 or 12, respectively, a degasser for removing gas from the liquid and/or a photodetector for measuring the energy of every single radiation pulse. The mentioned fiber bundle 2b or 16, respectively, may be followed by focusing or collimating lenses or prisms.

Although not explicitly stated, the casing 1b together with the transducer array 1a of the embodiments shown in FIGS. 11 to 14 can be movably mounted in the encasement 7 such that the array 1a can be moved toward and/or away from the object under investigation, whereby the distance between the transducer elements and the object and therefore the region of interest on or within the object can be varied. For this purpose, a moving mechanism is provided for moving the transducer array 1a and/or the illumination unit 2b, i.e. the end of the fiber bundle 2b, back and forth similar to the moving mechanism 19 shown in FIG. 6, 9 or 10, respectively. The elucidations given above with respect to FIGS. 5, 6, 9 and 10, for example, those regarding the intersection point P of the surface normals 21 and the light cone 20, apply accordingly.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A handheld device for optoacoustic imaging of an object, the handheld device comprising:
   an irradiation unit configured to irradiate a region on or within the object with electromagnetic radiation;
   a detector unit configured to detect acoustic waves generated in the object upon irradiation with electromagnetic radiation, the detector unit comprising an array of at least 128 detector elements and a curved surface forming a recess,
      wherein the irradiation unit is disposed in the recess,
      wherein the array of detector elements is arranged in a line along an arc on the curved surface, and
      wherein the detector elements are arranged in the recess such that the surface normals of at least a part of the detector elements are directed to a region of interest of the object and intersect at an intersection point located in the region of interest;
   wherein the irradiation unit is designed such that the irradiated region on or within the object coincides or overlaps with the intersection point of the surface normals of the detector elements; and
   a cover element that seals the curved surface on which the array of detector elements is provided such that the curved surface together with the cover element form a closed cavity that accommodates a coupling medium.

2. The handheld device according to claim 1, wherein the electromagnetic radiation comprises light.

3. The handheld device according to claim 1, wherein the acoustic waves comprise ultrasonic waves.

4. The handheld device according to claim 1, further comprising a container or an encasement, wherein the container or the encasement has a distal end, wherein the curved surface terminates at the distal end of the container or the encasement such that an open end of the recess is at the distal end of the container or the encasement, and wherein the cover element is provided at the distal end of the container or the encasement to seal the recess.

5. The handheld device of claim 4, wherein the cover element is mechanically flexible and is filled with a coupling medium to define a cushion configured to adapt to a variety of surface topologies of the object.

6. The handheld device of claim 4, wherein the handheld device comprises the encasement, wherein the encasement comprises an indentation that is sealed with the cover element, and wherein the cover element comprises a mechanically flexible membrane such that a section of the membrane in the region of the indentation exhibits an indentation to follow a surface curvature of the object and to permit the object to be positioned in the indentation of the membrane.

7. The handheld device according to claim 1, wherein the irradiation unit comprises a fiber bundle connected to a light source.

8. The handheld device according to claim 1, wherein the coupling medium comprises water.

9. The handheld device according to claim 1, wherein the region of interest of the object is located either around the cover element or beyond the cover element.

10. The handheld device according to claim 1, wherein the cover element comprises a mechanically flexible element.

11. The handheld device according to claim 10, wherein the cover element comprises a membrane or a film.

12. The handheld device according to claim 1, wherein at least a section of the cover element has a convex shape.

13. The handheld device according to claim 1, wherein the cover element is configured such that at least a section of the cover element comes into contact with the object while images are acquired from the object.

14. The handheld device according to claim 1, wherein at least one conveyance unit is provided for conveying the coupling medium into and/or out of the recess.

15. The handheld device according to claim 1, wherein the array of detector elements is a curved two-dimensional array of detector elements.

16. The handheld device according to claim 1, wherein the irradiation unit comprises a light source.

17. The handheld device according to claim 1, wherein the irradiation unit comprises one or more of an end face of a fiber bundle, lenses, or prisms.

18. The handheld device according to claim 1, wherein the irradiation unit is disposed at the curved surface of the recess.

19. The handheld device according to claim 1, wherein at least a section of the curved surface of the recess is configured such that reflection of acoustic waves incident on the curved surface of the recess towards the array of detector elements is reduced or avoided.

20. The handheld device according to claim 1, wherein at least one of:

A- the curvature;
B- the size; and
C- the angular coverage of the array of detector elements
depends on at least one of:
A- the size of the object and
B- the region of interest of the object.

21. A method for optoacoustic imaging of an object comprising:
irradiating a region on or within the object with electromagnetic radiation by an irradiation unit; and
detecting acoustic waves, which are generated in the object upon irradiation with electromagnetic radiation, by an array of at least 128 detector elements, wherein the irradiation unit is disposed in a recess that is formed by a curved surface, wherein the array of detector elements is arranged in a line along an arc on the curved surface and the detector elements are arranged in the recess such that the surface normals of at least a part of the detector elements are directed to a region of interest of the object and intersect at an intersection point located in the region of interest, wherein the irradiated region on or within the object coincides or overlaps with the intersection point of the surface normals of the detector elements, and wherein a cover element seals the curved surface on which the array of detector elements is provided such that the curved surface together with the cover element form a closed cavity that accommodates a coupling medium.

22. The method of claim 21, wherein the electromagnetic radiation comprises light.

23. The method of claim 21, wherein the acoustic waves comprise ultrasonic waves.

24. The method of claim 21, wherein said irradiating and detecting are accomplished via a handheld device that comprises a container or an encasement, wherein the container or the encasement has a distal end, wherein the curved surface terminates at the distal end of the container or the encasement such that an open end of the recess is at the distal end of the container or the encasement, and wherein the cover element is provided at the distal end of the container or the encasement to seal the recess.

25. The method of claim 24, wherein the cover element is mechanically flexible and is filled with a coupling medium to define a cushion configured to adapt to a variety of surface topologies of the object.

26. The method of claim 24, wherein the handheld device comprises the encasement, wherein the encasement comprises an indentation that is sealed with the cover element, and wherein the cover element comprises a mechanically flexible membrane such that a section of the membrane in the region of the indentation exhibits an indentation to follow a surface curvature of the object and to permit the object to be positioned in the indentation of the membrane.

* * * * *